US012733726B2

(12) United States Patent
Stiehl et al.

(10) Patent No.: US 12,733,726 B2
(45) Date of Patent: Sep. 15, 2026

(54) ROTARY BRUSH FOR WOUND CARE

(71) Applicants: James Bowen Stiehl, Salem, IL (US); Kurt R. Stiehl, Los Gatos, CA (US)

(72) Inventors: James Bowen Stiehl, Salem, IL (US); Kurt R. Stiehl, Los Gatos, CA (US)

(*) Notice: Subject to any disclaimer, the term of this patent is extended or adjusted under 35 U.S.C. 154(b) by 1098 days.

(21) Appl. No.: 17/158,687

(22) Filed: Jan. 26, 2021

(65) Prior Publication Data

US 2021/0227952 A1 Jul. 29, 2021

Related U.S. Application Data

(60) Provisional application No. 62/966,246, filed on Jan. 27, 2020.

(51) Int. Cl.
*A45D 34/04* (2006.01)
*A61B 17/32* (2006.01)

(52) U.S. Cl.
CPC ............ *A45D 34/042* (2013.01); *A61B 17/32* (2013.01); *A45D 2200/1018* (2013.01); *A45D 2200/1054* (2013.01); *A61B 2017/320012* (2013.01)

(58) Field of Classification Search
CPC .......... A45D 34/042; A45D 2200/1018; A45D 2200/1054; A61B 17/32; A61B 2017/320012; A61B 17/54; A61B 2017/00761; A61B 90/70; A61B 90/00; A46B 5/0095; A46B 9/005; A46B 11/063; A46B 13/008; A46B 2200/405; A46B 13/04; A46B 5/0066; A46B 13/023; A46B 15/0004; A46B 15/0034; A46B 2200/1006; A46B 2200/3073; A46B 13/02; A61L 2/10; A61M 1/00
See application file for complete search history.

(56) References Cited

U.S. PATENT DOCUMENTS 5,312,813 A 5/1994 Costerton et al.
5,624,419 A * 4/1997 Ersek ................. A61M 3/0287 604/304
5,921,251 A 7/1999 Joshi
5,953,783 A 9/1999 Hahn
6,090,085 A 7/2000 Mehl et al.
6,099,309 A * 8/2000 Cardarelli ............ A61C 17/005 433/125
7,306,569 B2 12/2007 Lajoie et al.
7,540,680 B2 6/2009 Feldman et al.
8,076,117 B2 12/2011 Trampuz et al.
(Continued)

OTHER PUBLICATIONS

Aseptico, AEU-425CF/CFH Transport II MDS Portable Dental System Operation and Maintenance Manual, Nov. 2016, Aseptico Inc., pp. 1-14 (Year: 2016).*
(Continued)

*Primary Examiner* — Tan-Uyen T Ho
*Assistant Examiner* — Osama Nemer
(74) *Attorney, Agent, or Firm* — Foley & Lardner LLP

(57) ABSTRACT

Systems, methods, and devices for debridement of wounds are described herein. A wound care system is disclosed. The wound care system includes a rotary brush, a fluid delivery system, and a control unit. The rotary brush is configured to brush a wound. The fluid delivery system is configured to rinse the wound. The control unit is configured to control a spin rate of the rotary brush and a fluid flow rate of the fluid delivery system.

17 Claims, 10 Drawing Sheets

(56) References Cited

U.S. PATENT DOCUMENTS 8,308,702 B2 11/2012 Batchvarova et al.
9,402,803 B2 * 8/2016 Archambeau .......... B01F 23/41
9,635,927 B2 5/2017 Godin et al.
10,080,428 B2 9/2018 Kern
10,149,735 B2 12/2018 Noell et al.
D836,919 S 1/2019 Cooper
10,173,247 B2 1/2019 Kalfe
10,188,194 B2 1/2019 Kim
D839,601 S 2/2019 Fang
2001/0018061 A1 8/2001 Rhoades
2003/0008588 A1 1/2003 Kohlruss et al.
2004/0083569 A1 * 5/2004 Kweon .................. A46B 9/045 15/167.1
2005/0043653 A1 2/2005 Trimmer et al.
2007/0160958 A1 * 7/2007 Belikov ............... A61C 19/066 433/215
2008/0146991 A1 * 6/2008 Hernandez .......... A61M 3/0266 604/113
2009/0062815 A1 * 3/2009 Karasiuk ................ A45D 34/04 606/131
2014/0020197 A1 * 1/2014 Nakamura ................ D01F 6/62 15/160
2015/0010919 A1 * 1/2015 Feinberg ................. A61L 27/22 427/407.1
2015/0305945 A1 10/2015 Engl et al.
2016/0058526 A1 * 3/2016 Policicchio .......... A61C 1/0084 433/29
2016/0157974 A1 * 6/2016 Zhang ................ A61C 17/0202 601/165
2017/0246351 A1 * 8/2017 Murthy ................... A61L 27/58
2017/0332776 A1 * 11/2017 Hughes, Jr. ............ A46B 17/08
2020/0330270 A1 * 10/2020 Foster .................... A46B 9/005
2021/0121386 A1 * 4/2021 Labib ....................... A61K 8/25

OTHER PUBLICATIONS

Aseptico, "Leading the Way in Portable Dentistry!", Sep. 1, 2007, Journal of Public Health Dentistry, vol. 67, No. 5, p. 23 (Year: 2007).*

* cited by examiner

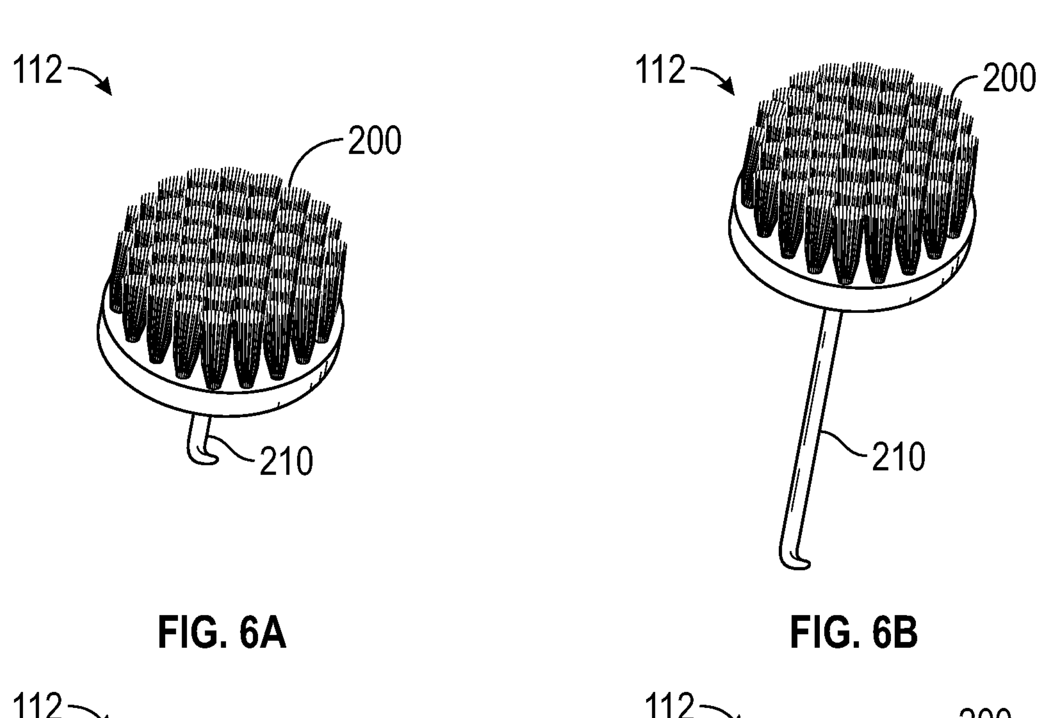
FIG. 6A
FIG. 6B
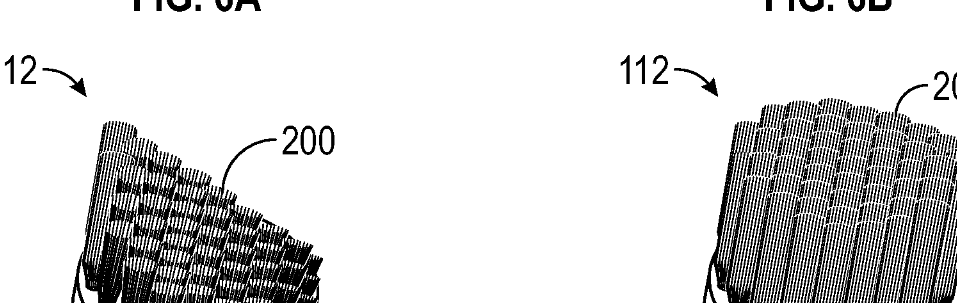
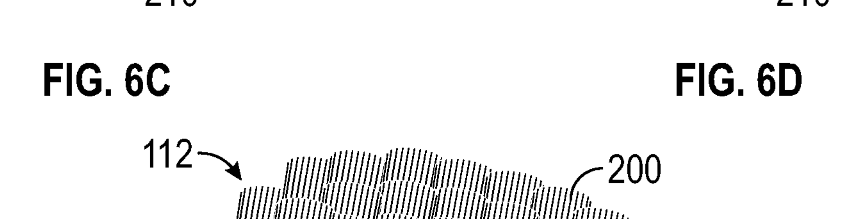
FIG. 6C
FIG. 6D
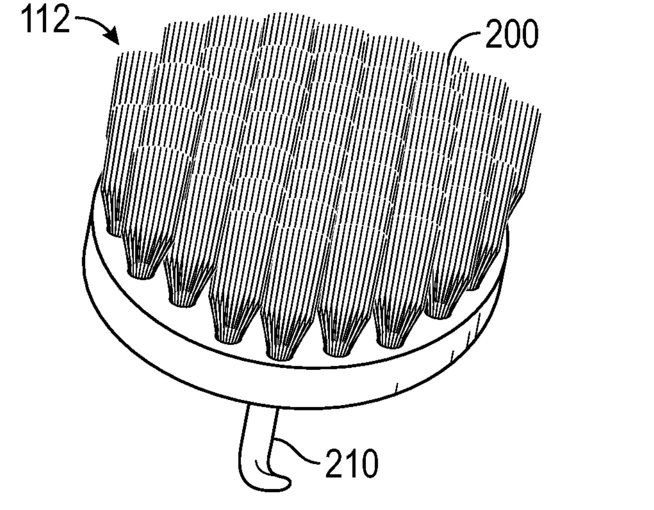
FIG. 6E

ROTARY BRUSH FOR WOUND CARE

CROSS-REFERENCE TO RELATED APPLICATION

This application claims the benefit of and priority to U.S. Provisional Application No. 62/966,246, filed Jan. 27, 2020, and titled "Rotary Brush for Wound Care," which is incorporated herein by reference in its entirety.

BACKGROUND

The present disclosure relates generally to wound care. More specifically, the present disclosure relates to the debridement of wounds. Debridement of wounds involves removing wound contaminants such as foreign debris, necrotic tissue, wound slough, bacteria, and bacterial extracellular polymeric substance, such as biofilm. Debridement of wounds, such as mechanical debridement, may involve applying a force to the surface of a wound in order to disrupt the surface of the wound to detach the biofilm from the substrate surface.

SUMMARY

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

In certain embodiments, a wound care kit is disclosed. The wound care kit includes a rotary brush configured to engage a wound; a fluid delivery device configured to deliver fluid to the wound, and a control unit configured to control the operation of the rotary brush.

In certain embodiments, a method of cleaning a wound is disclosed. The method includes brushing the wound using a rotary brush and rinsing the wound using a fluid delivery device.

In certain embodiments, a wound care system is disclosed. The wound care system includes a rotary brush configured to brush a wound, a fluid delivery system configured to rinse the wound, and a control unit configured to control spin rate of the rotary brush.

BRIEF DESCRIPTION OF THE DRAWINGS

FIG. 6A is a side view of a brush head according to an example embodiment.

FIG. 6B is a side view of a brush head according to another example embodiment.

FIG. 6C is a side view of a brush head according to another example embodiment.

FIG. 6D is a side view of a brush head according to another example embodiment.

FIG. 6E is a side view of a brush head according to another example embodiment.

DETAILED DESCRIPTION

Figure 1:
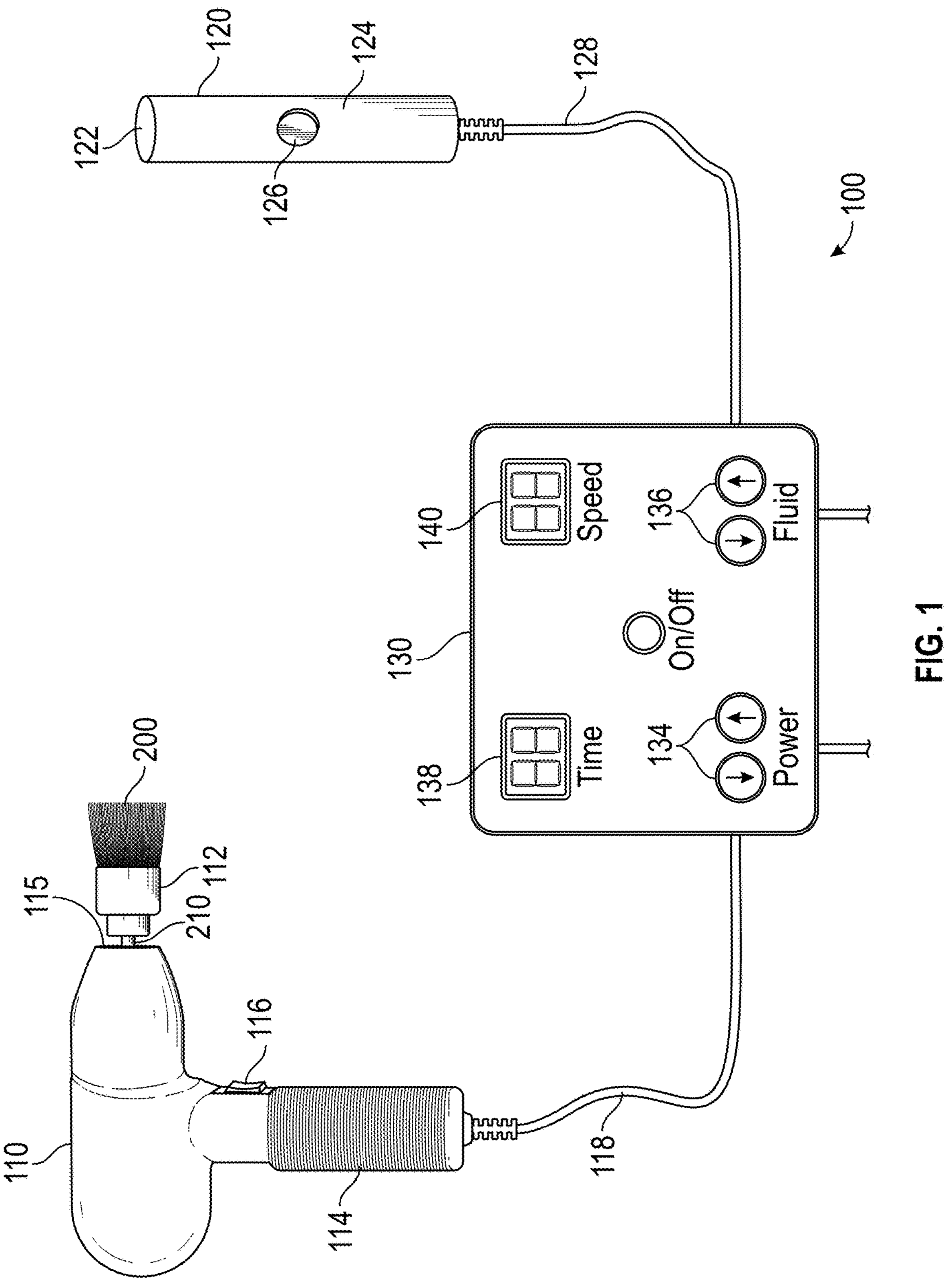
FIG. 1 is a perspective view of a debridement system according to an example embodiment.

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Biofilm may include any syntrophic consortium of microorganisms in which cells stick to each other and also to a surface. The adhesive and cohesive nature of these cells cause the cells to become embedded within a slimy extracellular matrix that includes bacterial extracellular polymeric substances. The cells within the biofilm produce the extracellular polymeric substances, which are typically a polymeric conglomeration of extracellular polysaccharides, proteins, lipids, and DNA. This bacterial extracellular polymeric substance is produced by at least 80% of all bacterial species in chronic wounds as a response to the harsh environment created by the human inflammatory mechanism.

Biofilm can be a dense sticky material that tends to harbor bacteria and protect the bacteria from external agents such as antibiotics, antiseptics, and antibodies. Bacteria are stimulated by neighboring bacteria to become phenotypically dormant or non-reproductive via a polypeptide trigger. The "quorum sensing factor," where the bacteria are stimulated to harbor in small communities, enables the bacteria to become antibiotic tolerant. Bacteria deep in the biofilm matrix is protected from antiseptics, as the antiseptic substances are quickly bound to the biofilm surface and cannot reach the deepest levels of the biofilm.

A buildup of biofilm on the surface of a wound may significantly hinder the healing process. The human body attempts to combat the adverse effects of biofilm and bacteria on the surface of a wound. For example, the human complement system may recognize DNA fragments in the bacteria and stimulate the migration of neutrophils and mast cells to the wound site to attack biofilm and bacteria. Further, proteases are created and released in higher than normal levels to break down the biofilm. However, the human body is often unsuccessful in combating biofilm, and medical treatment is frequently needed.

Biofilm may be semi-permeable or permeable, allowing for substances like biocides and surfactants to penetrate the surface of the biofilm. For example, disruption of the biofilm attachment and extracellular polymeric substance matrix may be accomplished using surfactants such as benzalkonium, Pluronic F127, or betaine. While surfactants may facilitate loosening the biofilm, additional debridement is often needed to further combat biofilm in chronic wounds.

One method of managing biofilm involves applying antibiotics and antiseptics to the surface of the wound. However, antiseptics may have limited access to persistor bacteria found in the deepest layers of the biofilm mass. This relates to the highly reactive chemical activity of biocides that are reduced near the surface of the biofilm and never reach the deepest layers of the biofilm. This reaction diffusion effect leads to increasing antiseptic solution concentration, which may reach a level that becomes toxic to human cells. For example, highly reactive antiseptics like hypochlorous acid may be used in an attempt to combat biofilm. While the antiseptic quickly reacts with biofilm surface structures, this antiseptic does not effectively combat the biofilm at the deepest layers of the biofilm. This is, in part, due to the structure of the biofilm and the reaction-diffusion effect between the antiseptic and the biofilm that results in a low concentration of antiseptic reaching the deepest layers of the biofilm. Similarly, topical antibiotics may not effectively combat biofilms at the deepest layers of the biofilm.

Using a hydrogen peroxide base may facilitate penetration of the biofilm. This concept, referred to as a "microbubbler," uses a hydrogen peroxide base to penetrate the biofilm, which is then chemically catalyzed by manganese dioxide producing oxygen bubbles that may disrupt the biofilm. However, using a hydrogen peroxide base may not disrupt the deepest levels of the biofilm.

Another method of managing biofilm is through mechanical debridement. Mechanical debridement of wounds, especially deep wounds, may allow the human immune system to stabilize the wound, enabling and/or accelerating the healing process. For example, debridement of wounds may accelerate the healing process for invasive wounds such as diabetic ulcers, decubitus ulcers, arterial and venous ulcers, traumatic wounds, and postoperative wounds, all of which may become infected due to bacterial contamination.

Mechanical debridement may involve scraping or cutting away the biofilm and the surrounding infected flesh. In general, this requires a surgeon to physically remove debris, dead tissue, contaminated bone, and the products of chronic inflammations/infection. Scraping and cutting away biofilm and the surrounding areas is typically done in the operating room with anesthesia if sharp debridement is required. Sharp debridement can be a painful and time intensive process.

Mechanical jet saline lavage, a form of mechanical debridement, which involves using pressurized fluid to remove the biofilm, may also be used to clean a wound. Mechanical jet saline lavage, used in combination with surfactants, may effectively loosen the biofilm attached to the wound. While mechanical jet saline debridement may be less painful than scrapping or cutting away the biofilm, this method may only be effective against minor wounds with little biofilm. These types of wounds often do not require repeated sharp debridement and simply cleansing the wound is all that is needed.

Once the biofilm has been loosened, wound cloths may be used to wipe the wound surface in order to remove the substrate loosened biofilm, which may effectively remove some of the bacteria and biofilm from the wound. However, the amount of force needed to remove the biofilm without damaging the underlying fragile granulation tissue is unknown and variable. More broadly, the strength of biofilm attachment to the substrate is ubiquitous. Factors such as biofilm shape, underlying substrate features, stage, and status of the bacteria biofilm community all influence the strength of the biofilm attachment to the substrate.

Referring now to FIG. 1, a wound care system 100 is shown according to an example embodiment. The wound care system 100, and all other systems, methods, and kits disclosed herein, may be used in addition to, or in lieu of, any of the above identified biofilm management techniques. According to this example embodiment, the wound care system 100 includes a rotary brush 110 (e.g., an electric powered rotary brush), a fluid delivery device 120 (e.g., an electric powered irrigation device), and a control unit 130. In this embodiment, the control unit 130 is configured to control operation a brush head 112 (e.g., the spin rate) and the fluid flow rate through a tip 122 of the fluid delivery device 120, as will be discussed in more detail below. Both the rotary brush 110 and the fluid delivery device 120 may be controlled independently, as will be discussed in further detail.

In certain embodiments, the control unit 130 may be used to control the rotary brush 110. For example, the control until 130 may have brush controls 134, capable of receiving input from an operator. For example, an operator of the control unit 130 may increase the spin rate of the brush head 112 by pressing one of the brush controls 134, and may decrease the spin rate of the brush head 112 by pressing the other brush control 134. The spin rate of the brush head 112 may be displayed on a speed display 140 on the control unit 130.

Further, the control unit 130 may be used to control the fluid flow rate through the tip 122 of the fluid delivery device 120. For example, a user may press one of the fluid controls 136 to increase the fluid flow rate through the tip 122, and the user may press the other fluid control 136 to decrease the fluid flow rate through the tip 122. The control until 130 may also include a display that displays the fluid flow rate through the tip 122.

The control unit 130 may further include a time display 138. The time display 138 may display how long the brush head 112 has been spinning and/or how long fluid has been getting ejected from the tip 122. Further, the control unit 130 may be preset to spin the brush head 112 for a predetermined amount of time and/or eject fluid from the tip 122 for a predetermined amount of time. The time display 138 may display the time elapsed and/or remaining for either of these actions. In certain embodiments, the control unit 130 has a standard 110/220 volt electronic interface. It should be appreciated that the control unit 130 may communicate with the rotary brush 110 using a power cord 118, or the control unit 130 may wirelessly communicate with a battery powered rotary brush 110. Similarly, the control unit 130 may wirelessly control the fluid delivery device 120.

Figure 2:
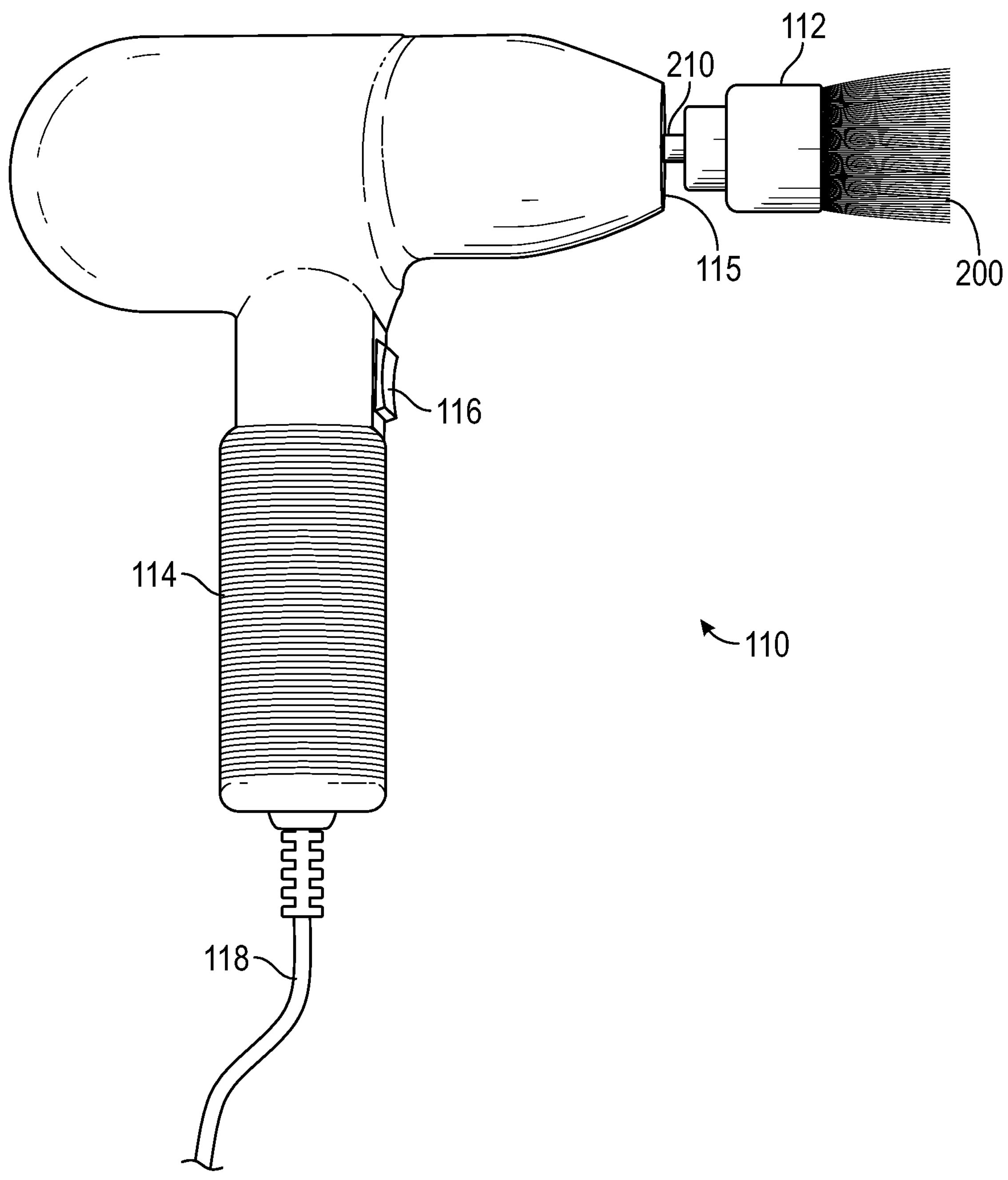
FIG. 2 is a perspective view of a rotary brush according to an example embodiment.

As shown in the example embodiment in FIG. 2, the rotary brush 110 may include a brush head 112, a handle 114, a brush head interface 115, a control mechanism 116, and a power cord 118. In this example embodiment, the brush head 112 includes a plurality of bristles 200 and a rotary shaft 210. The brush head interface 115 is configured to receive the rotary shaft 210 of the brush head 112, such that the rotary shaft 210 may rotate within the brush head interface 115. Further, the control mechanism 116 may be configured to control the brush head 112. For example, in the embodiment shown in FIG. 2, the control mechanism 116 is a trigger that may be pressed by an operator while the operator is holding the rotary brush by the handle 114. When the control mechanism 116 is pressed, the rotary brush 110 may be turned on, causing the rotary shaft 210 to spin, thereby causing the brush head 112 to spin. In this example embodiment, the rotary brush 110 is powered using an alternating current (AC) power cord 118 to power an electric motor that causes the rotary shaft 210 to rotate within the brush head interface 115. However, the rotary brush 110 may be powered in a number of ways, including a direct current power supply (DC), such as a battery built into the handle 114, compressed air, or an electronic impulse that comes from a free standing control box.

Figure 3:
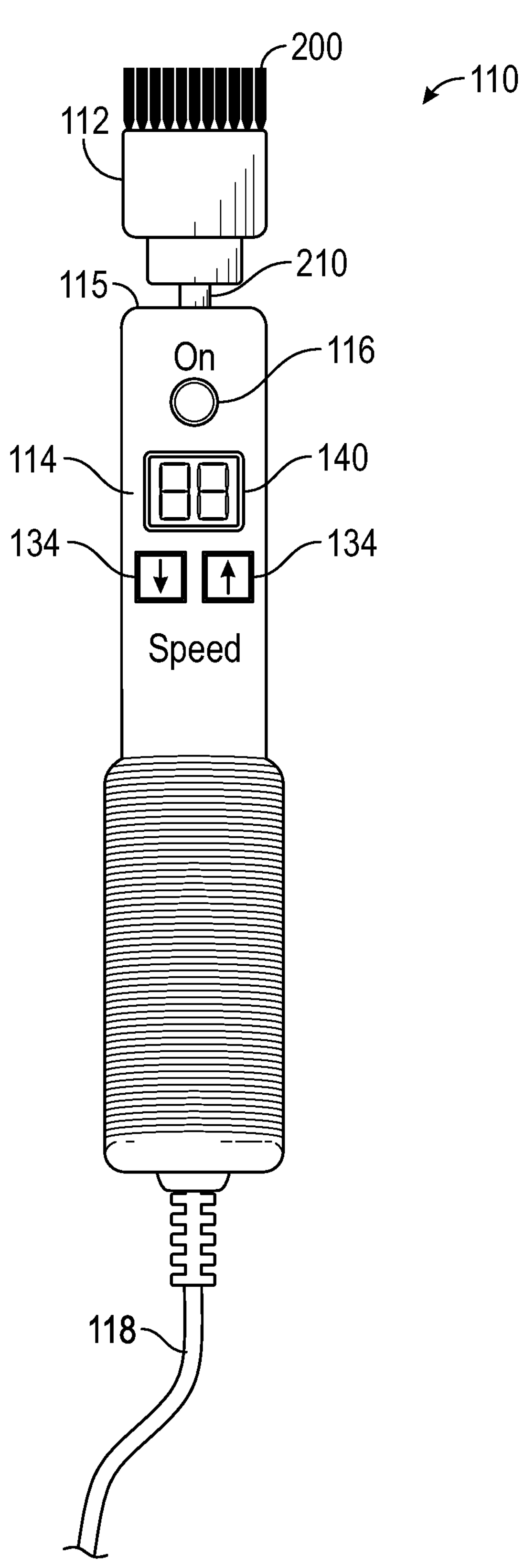
FIG. 3 is a perspective view of a rotary brush according to another example embodiment.

Referring now to FIG. 3, a rotary brush 110 is shown according to another example embodiment. In this example embodiment, the rotary brush 110 includes a brush head 112, a handle 114, a brush head interface 115, a control mechanism 116, a power cord 118, brush controls 134, and a speed display 140. In this example embodiment, the brush head 112 includes a plurality of bristles 200 and a rotary shaft 210. The brush head interface 115 is configured to receive the rotary shaft 210 of the brush head 112, such that the rotary shaft 210 may rotate within the brush head interface 115. Further, the control mechanism 116 may be configured to control the brush head 112. For example, in the example embodiment shown in FIG. 3, the control mechanism 116 is a button configured to receive input from an operator. For example, when the control mechanism 116 is pressed and released, the rotary brush 110 may be turned on, causing the rotary shaft 210 to spin, thereby causing the brush head 112 to spin.

In this example embodiment, the rotary brush 110 is powered using an alternating current (AC) power cord 118 to power an electric motor that causes the rotary shaft 210 to rotate within the brush head interface 115. However, the rotary brush 110 can be powered in a number of ways, including a direct current power supply (DC), such as a battery built into the handle 114, compressed air, or an electronic impulse that comes from a free standing control box.

In certain embodiments, the rotary brush 110 may utilize a servo-activating system with variable input to control the spin rate of the brush head 112. The rotary brush 110 may further include an on/off switch, and digital readouts that measure the spin rate of the brush head 112, for example, in rotations per minute (RPMs). Further, the rotary brush 110 may include a force sensor that measures the force on the brush head 112 when the brush head is pressed against a wound. In certain embodiments, the force sensor may be coupled to a display that displays the force being applied by the brush head 112 to a wound. In certain embodiments, the rotary brush 110 may automatically stop spinning the brush head 112 in response to the force sensor measuring a force over a predetermined threshold. This feature may help prevent the brush head 112 from damaging the wound.

The rotary brush 110 shown in FIG. 3 may further be controlled using the brush controls 134 located on the handle 114. For example, the brush controls 134 may include a plurality of buttons. One of the buttons may be pressed by an operator to increase the spin rate of the brush head 112, and another one of the buttons may be pressed by an operator to decrease the spin rate of the brush head 112. For example, an operator may set a spin rate of eight-hundred rotations per minute (RPMs) for the brush head 112 using the brush controls 134. In certain embodiments, the spin rate of the brush head may be displayed on the speed display 140. In this example embodiment, a control unit 130 may not be needed to control the rotary brush 110 since the rotary brush includes the control mechanism 116 and the brush controls 134.

Figure 4:
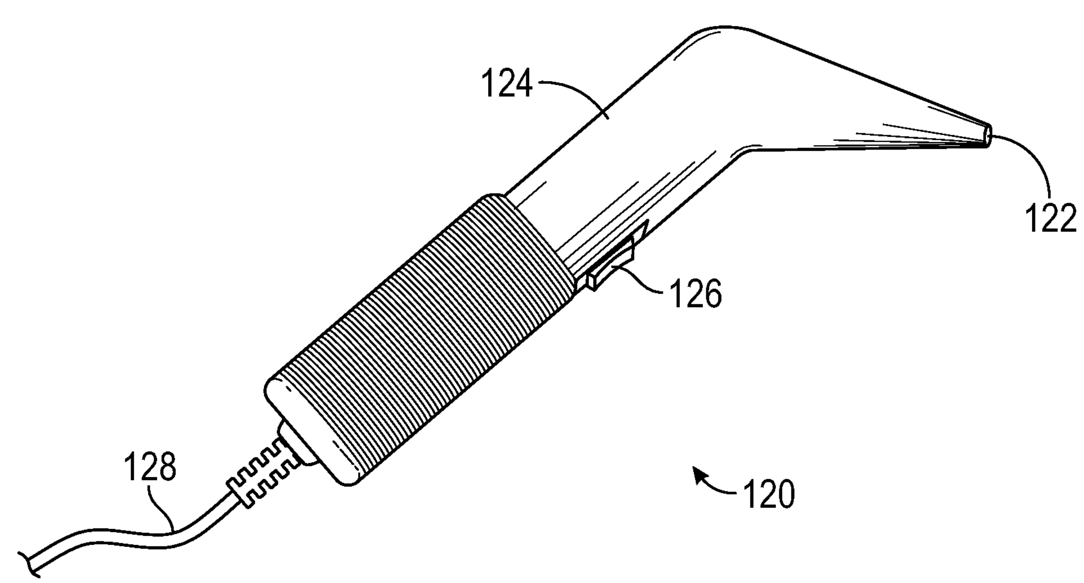
FIG. 4 is a perspective view of a fluid delivery device according to an example embodiment.

Referring now to FIG. 4, a fluid delivery device 120 is shown according to an example embodiment. The fluid delivery device 120 may include a tip 122, a handle 124, a control mechanism 126, and a supply line 128. In this example embodiment, the supply line 128 may provide a fluid, such as water or a saline solution, to the fluid delivery device 120. An operator may use the handle 124 to hold the fluid delivery device 120 and the control mechanism 126 to control the fluid delivery device 120. In this example embodiment, the control mechanism 126 is a trigger mechanism used to activate the fluid delivery device 120. For example, when an operator presses the control mechanism 126, a fluid may be ejected from the tip 122 in a desired direction.

Figure 5:
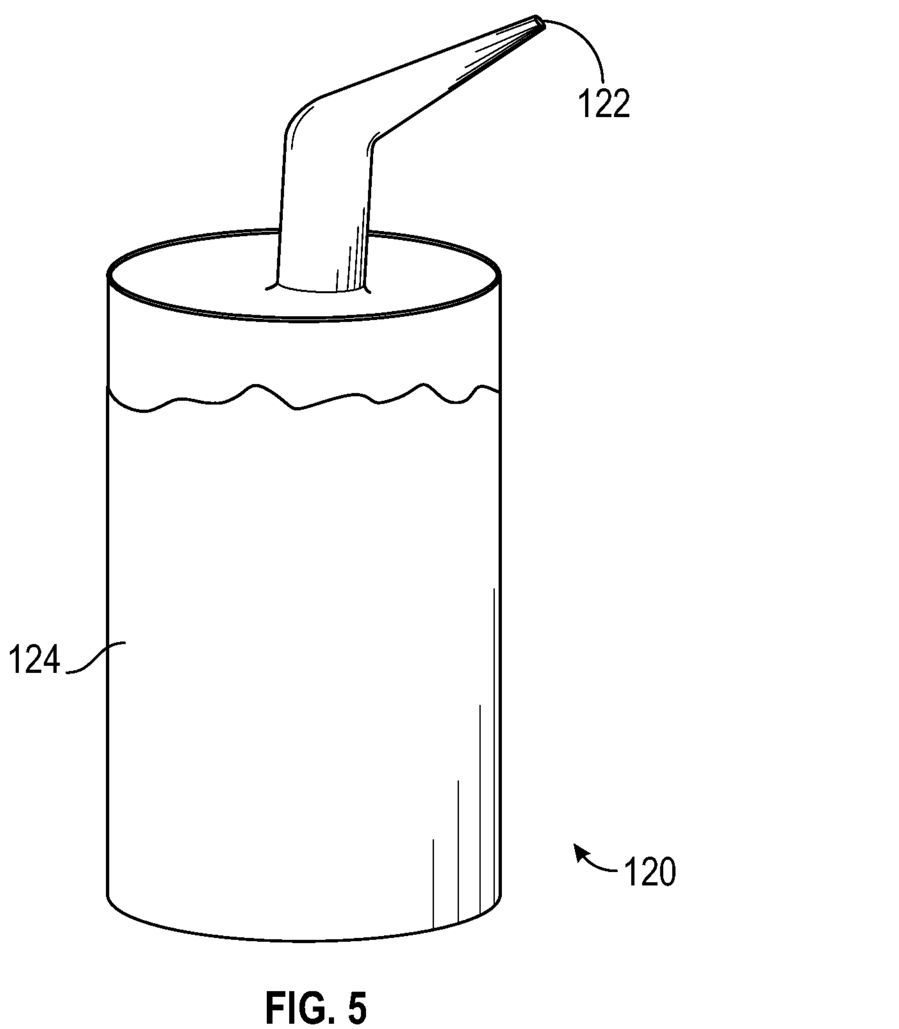
FIG. 5 is a perspective view of a fluid delivery device according to another example embodiment.

Referring now to FIG. 5, a fluid delivery device 120 is shown according to another example embodiment. In this example embodiment, the fluid delivery device 120 is a squirt bottle having a handle 124 and a tip 122. The fluid delivery device 120 may be filled with a fluid, such as water or a saline solution. In this example embodiment, the fluid delivery device 120 may be held by an operator at the handle 124. When the operator applies pressure to the handle 124, fluid may be ejected from the tip 122 in a desired direction. In this example embodiment, a control until 130 may not be needed to control the fluid delivery device 120. Alternatively, the fluid delivery device may be a syringe.

Referring now to FIGS. 6A-6J, a brush head 112 is shown according to several example embodiments. The brush heads 112 include a rotary shaft 210 that is configured to be received by the brush head interface 115 of the rotary brush 110 (see FIG. 2). The brush head interface 115 may then engage the rotary shaft 210 such that rotary shaft 210 can spin within the brush head interface 115. Since the brush head 112 may be removable from the brush head interface 115, a variety of different brush heads 112 may be used with the same rotary brush 110. For example, the brush heads 112 shown in FIGS. 6A and 6B have rotary shafts 210 of different lengths. The operator may select the brush head 112 with a rotary shaft 210 having a certain length based on the desired use of the rotary brush 110. For example, if an operator wishes to use the rotary brush 110 in certain hard to reach areas, the operator may choose a brush head 112 having an especially long rotary shaft 210. In certain embodiments, the rotary shaft 210 may have a length of one inch. In other embodiments, the rotary shaft 210 may have a length of up to eight inches.

In certain embodiments, each brush head 112 includes a universal snap lock that engages the brush head interface 115, such that the brush head 112 can be locked into the rotary brush 110. In certain embodiments, the brush head 112 may be locked into place using a chuck device secured with a key, a specialized coupling device, or a fixed connection.

Each brush head 112 may also include a plurality of bristles 200 of varying length. For example, bristles 200 of the rotary brush shown in FIG. 6A may be longer than the bristles shown in FIG. 6E. Additionally, the length of the bristles 200 may vary throughout the brush head 112. For example, the brush head 112 shown in FIG. 6C has bristles 200 that vary in length. Further, the plurality of bristles 200 may have different diameters in different brush heads 112. For example, one brush head 112 may have bristles 200 that have a diameter of about twenty microns, while another brush head 112 may have bristles 200 that have a diameter of about three-hundred fifty microns. Further, one brush head 112 may have several different diameters of bristles 200. For example, one brush head 112 may have bristles with a diameter of about two hundred microns, one-hundred fifty microns, one hundred microns, eighty microns, fifty microns, thirty microns, twenty microns, and fifteen microns.

Further, each brush head 112 may have a different bristle density (i.e. the number of bristles 200 per square inch). For example, the brush head 112 shown in FIG. 6I may have a lower bristle density than the brush head 112 shown in FIG. 6J. Generally speaking, a brush head 112 with a higher bristle density may be used to apply a greater force than a brush head 112 with a lower bristle density.

Further, each brush head 112 may have a different diameter. For example the brush head 112 shown in FIG. 6I may have a larger diameter than the brush head 112 shown in FIG. 6J. A brush head 112 with a smaller diameter may be selected for smaller wounds, such as a wound on a hand or foot, while a brush head with a larger diameter may be used for larger wounds. In certain embodiments, the bristle 200 area of the brush head 112 may range from 1500 $mm^2$ to 7500 $mm^2$. Further, the bristles 200 of each brush head 112 may be made of different materials. For example, the bristles 200 of a brush head 112 may be made of polypropylene or nylon.

Figure 6F:
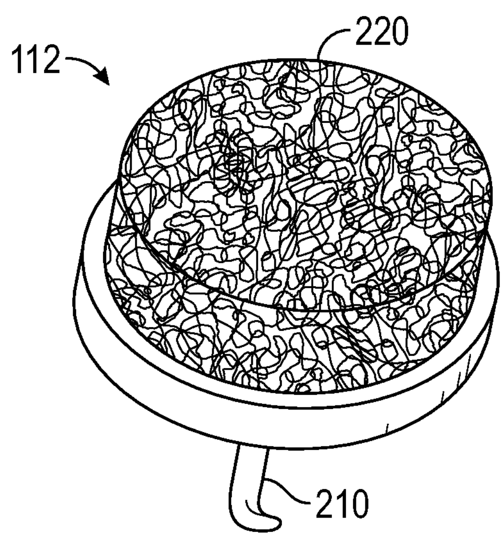
FIG. 6F is a side view of a brush head according to another example embodiment.
Figure 6G:
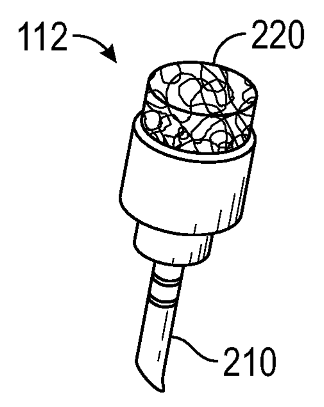
FIG. 6G is a side view of a brush head according to another example embodiment.
Figure 6H:
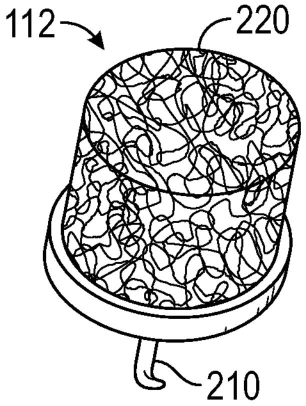
FIG. 6H is a side view of a brush head according to another example embodiment.
Figure 6I:
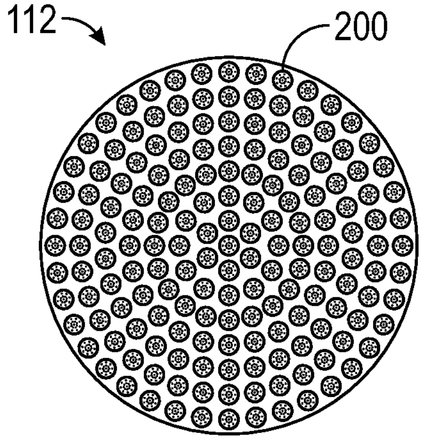
FIG. 6I is a top view of a brush head according to another example embodiment.
Figure 6J:
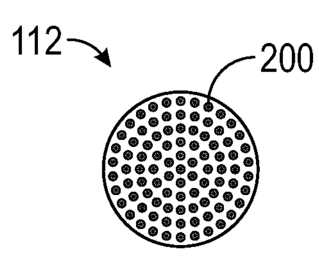
FIG. 6J is a top view of a brush head according to another example embodiment.

In further embodiments, such as the embodiments shown in FIGS. 6F-H, the brush head 112 may include a pad 220 instead of bristles. For example, the pad may be made of smooth plastic foam or felt. An operator may use a brush head with a pad 220 instead of bristles to clean metal surfaces or dense human tissue such as cortical bones. In certain embodiments, the pad may have a surface area of 1500 $mm^2$ to 7500 $mm^2$.

In certain embodiments, multiple brush heads 112 may be bundled together in a wound care kit. For example, the wound care kit may include all of, or any combination of, the brush heads 112 shown in FIGS. 6A-6J. The wound care kit may also include other brush heads that vary in brush head 112 shape, brush head 112 diameter, rotary shaft 210 length, bristle 200 material, bristle 200 length, bristle 200 stiffness, bristle density, pad 220 material, pad 220 shape, pad 220 material, etc. The wound care kit may further include a rotary brush 110 with a rotary brush interface 115 configured to receive each of the different brush heads 112. The wound care kit may also include multiple different rotary brushes 110. For example, the wound care kit may include the rotary brush shown in FIG. 2 and the rotary brush shown in FIG. 3. The wound care kit may further include any other component discussed herein, including, but not limited to a fluid delivery device 120 and an enclosure device 320.

Figure 7:
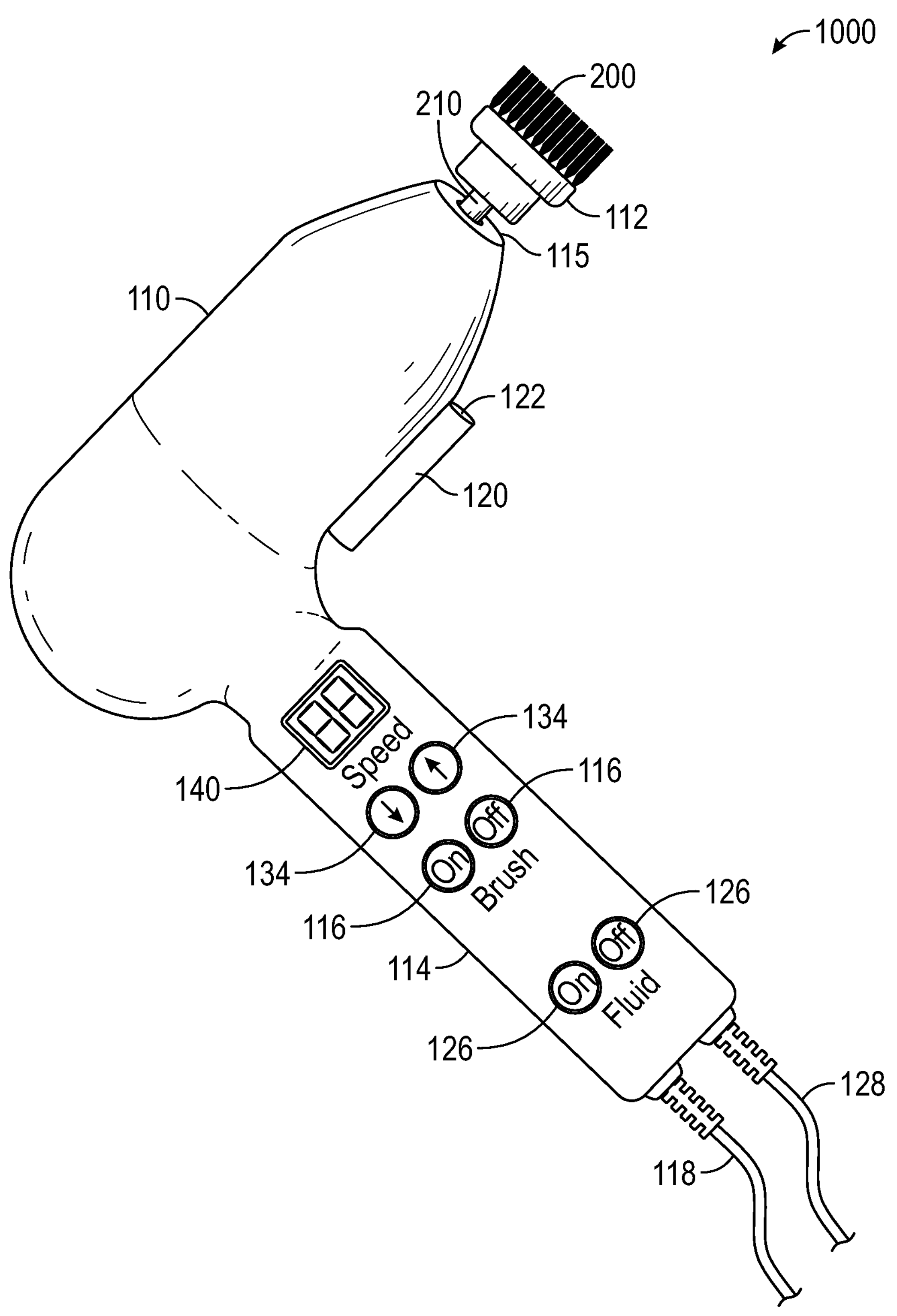
FIG. 7 is a perspective view of a debridement system according to another example embodiment.

Referring now to FIG. 7, a wound care system 1000 is shown according to another example embodiment. In this example embodiment, the rotary brush 110 and the fluid delivery device 120 are integrated into a single hand held device. This example wound care system 1000 includes a brush head 112, a handle 114, a brush head interface 115, a control mechanism 116, a power cord 118, brush controls 134, and a speed display 140.

In this example embodiment, a user may grip the wound care system 100 by the handle 114 and can cause the brush head 112 to spin using the control mechanism 116. For example, by pressing the control mechanism 116 labeled "ON," the user may cause the brush head 112 to spin, and by pressing the control mechanism 116 labeled "OFF," the user may stop the brush head 112 from spinning. Further, the user may customize the spin rate of the brush head 112 using the brush controls 134 to either increase or decrease the spin rate of the brush head 112. The spin rate of the brush head 112 may then be displayed on the speed display 140. In this example embodiment, the rotary brush 110 is powered using an alternating current (AC) power cord 118 to power an electric motor that causes the rotary shaft 210 to rotate within the brush head interface 115. However, the rotary brush 110 can be powered in a number of ways, including a direct current power supply (DC), such as a battery built into the handle 114, compressed air, or an electronic impulse that comes from a free standing control box.

Further, in the example embodiment shown in FIG. 7, the wound care system 1000 includes a fluid delivery device 120. The fluid delivery device 120 may include a tip 122, a handle 114, control mechanisms 126, and a supply line 128. In this example embodiment, the supply line 128 may provide a fluid, such as water or a saline solution, to the fluid delivery device 120. An operator may use the handle 114 to hold the fluid delivery device 120 and the control mechanisms 126 to control the fluid delivery device 120. For example, in this example embodiment, the user may press the control mechanism 126 labeled "ON," to eject fluid from the tip 122 in a desired direction. Further, the user may press the control mechanism 126 labeled "OFF" to stop fluid from being ejected from the tip 122. Since the controls are built into the wound care system 1000, a separate control unit may not be needed.

Figure 8:
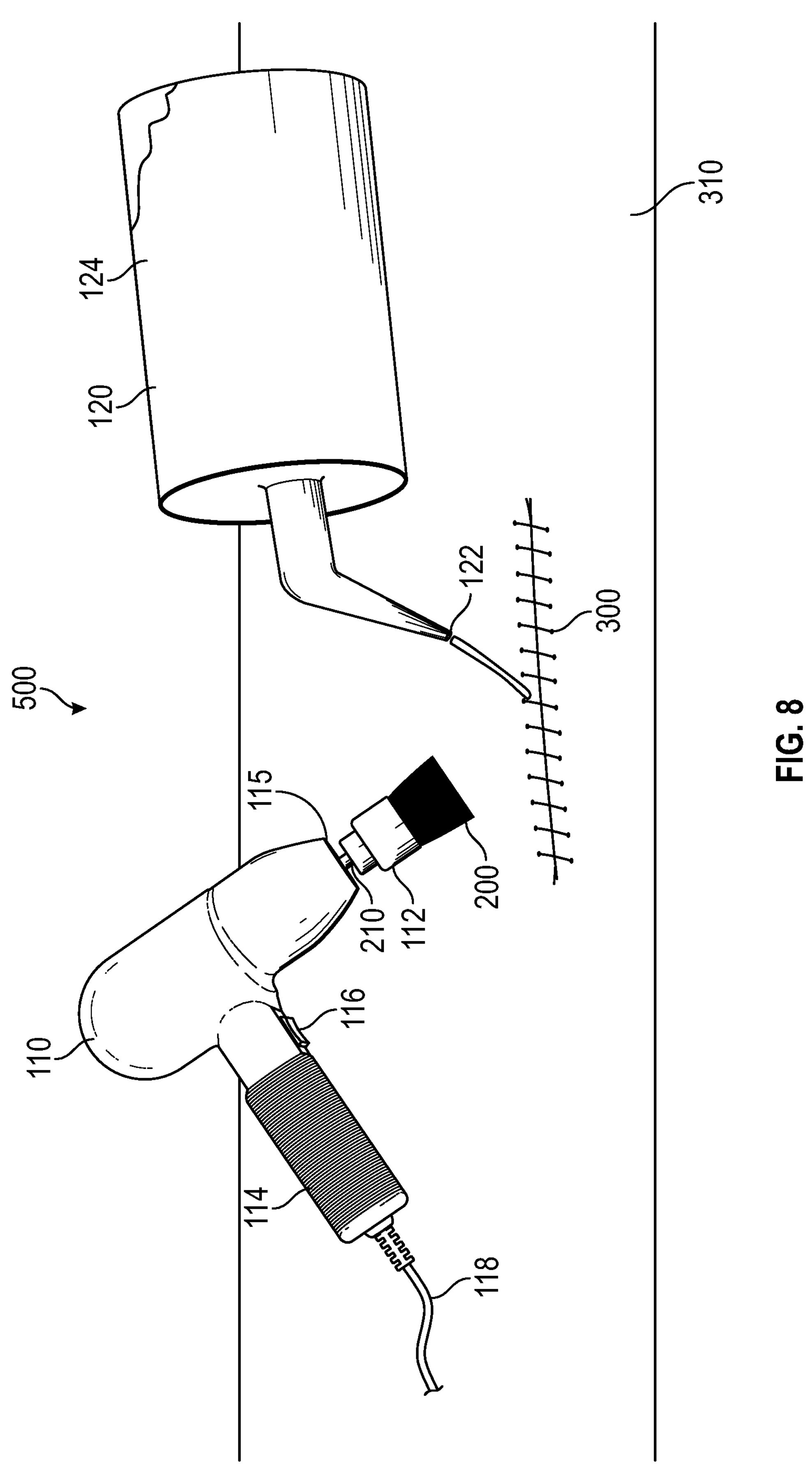
FIG. 8 is a perspective view of a biofilm treatment system according to an example embodiment.

Referring now to FIG. 8, a wound care system 500 is shown according to an example embodiment. For example, the wound care system 500 includes rotary brush 110 and a fluid delivery device 120. In this example embodiment, an operator may grab the rotary brush 110 by the handle 114. The user may then cause the brush head 112 to spin by pressing the control mechanism 116. Once the brush head 112 is spinning, the user may then use the brush head 112 to clean a wound 300. In this example embodiment, the wound 300 includes stiches in skin 310.

Further, in this example embodiment, the fluid delivery device 120 may be used to eject a fluid from the tip 122 in order to rinse the wound 300. In this example embodiment, the user may squeeze the handle 124 of the fluid delivery device 120 to eject a fluid, such as a saline solution, in a direction towards the wound 300.

Figure 9:
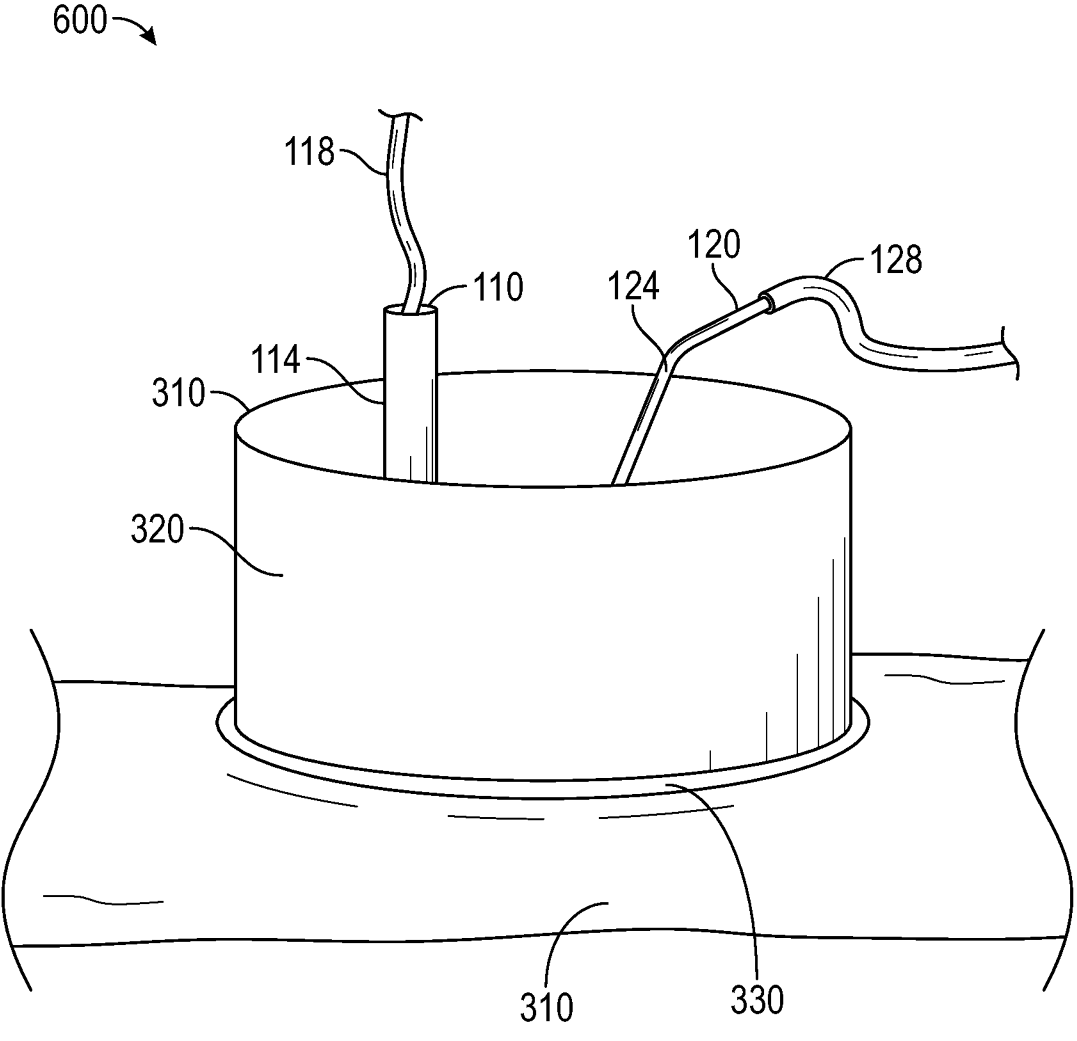
FIG. 9 is a perspective view of a biofilm treatment system according to another example embodiment.

Referring now to FIG. 9, a wound care kit 600 is shown according to an example embodiment. The wound care kit 600 includes a rotary brush 110 and a fluid delivery device 120. In this example embodiment, the wound care kit 600 also includes an enclosure device 320 (e.g., a cover, a tube, a sheet of material, a bag, etc.). In certain embodiments, the enclosure device 320 is made from a water resistant material, such as plastic. The enclosure device 320 may be secured to a portion of skin 310 using an adhesive 330, such that the enclosure device 320 will completely surround a wound. The enclosure device 320 is configured to receive the rotary brush 110 and the fluid delivery device 120 such that the enclosure device 320 encompasses the rotary brush 110 and the fluid delivery device 120. In certain embodiments, the enclosure device 320 may seal at a top portion 340 of the enclosure device 320, such that the rotary brush 110 and the fluid delivery device 120 are enclosed within the enclosure device 320. In certain embodiments, the wound care kit 600 may also include a suction device used to suck out any fluid and/or debris that are collected within the enclosure device 320.

In some embodiments, the handle 114 of the rotary brush 110 may be sealed outside of the enclosure device 320. In this example embodiment, the brush head 112 may include a rotary shaft 210 long enough to extend into the enclosure device 320, such that the brush head interface 115 is located outside of the enclosure device 320, while the bristles 200 are located inside the enclosure device 320. In this example embodiment, the enclosure device 320 may seal around the rotary shaft 210, thereby containing the fluid and aerosolization created by the fluid delivery device after the biofilm attached to the wound has been disrupted by the brush head 112.

In further embodiments, the handle 114 of the rotary brush 110 may be sealed outside of the enclosure device 320, while the brush head interface 115 and the brush head 112 are sealed inside the enclosure device 320. In this example embodiment, the enclosure device may seal around the rotary brush 110, such that the control mechanism 116 and any brush controls 134 that the rotary brush 110 may have are sealed outside of the enclosure device 320. This example embodiment allows an operator to access the control mechanism 116 and any brush controls 134 outside of the enclosure device 320, while containing the fluid and aerosolization created by the fluid delivery device after the biofilm attached to the wound has been disrupted by the brush head 112.

Figure 10:
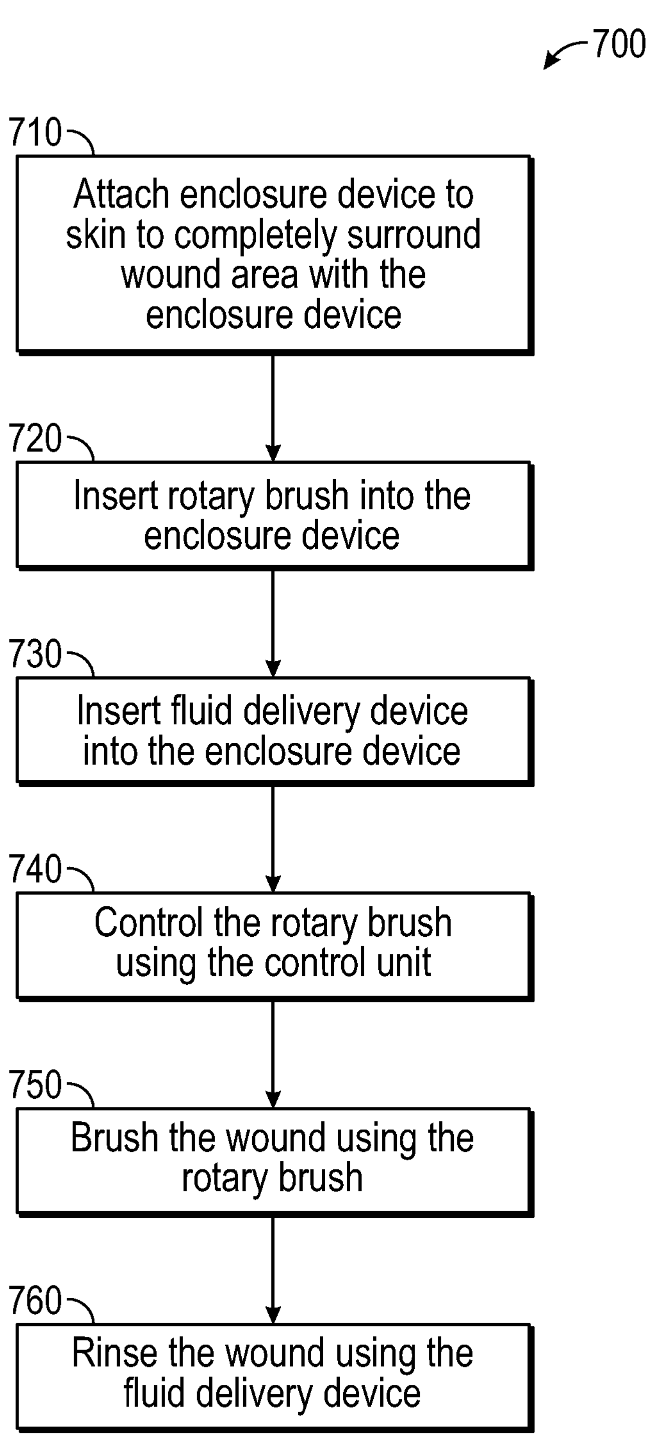
FIG. 10 is a flow chart diagram of a biofilm treatment method according to an example embodiment.

Referring now to FIG. 10, a flow chart for a method of cleaning a wound 700 is shown. According to one embodiment, the method of cleaning a wound 700 may include using a rotary brush to spin a sterile brush head to cleanse and remove the bacterial biofilm from the surface of a wound and the loosened debris may then be removed with a fluid delivery device. In certain embodiments, the fluid delivery device may be, or include, a low-pressure jet lavage surgical irrigation system. In certain embodiments, the method of cleaning a wound 700 may be used for removing bacterial biofilm in the clinical setting of chronic infection/inflammation. It should be appreciated that some steps shown in FIG. 10 may be omitted and further steps may be performed in various alternative embodiments.

At step 710, an enclosure device is attached to skin to surround a wound area with the enclosure device. For example, an adhesive may be used to secure the enclosure device to the skin. By doing so, any fluid sprayed onto the wound, and any aerosolization, debris, bacteria, and biofilm may be contained within the enclosure device.

At step 720, a rotary brush is inserted into the enclosure device. Step 730 involves inserting a fluid delivery device into the enclosure device. It should be noted that step 730 may also be performed prior to step 720, or step 720 and step 730 may be performed simultaneously. In certain embodiments, once both the rotary brush and the fluid delivery device are inserted into the enclosure device, the enclosure device may be sealed along an upper portion of the enclosure device, thereby encompassing the rotary brush and the fluid delivery within the enclosure device. For example, the rotary brush and fluid delivery device may be inserted into the enclosure device creating an enclosed irrigation enclosure device, providing a simple outpatient treating system, enhancing the sterility of the wound treatment process, and eliminating exposure of the patient and medical providers to diseases that may be transmitted by the aerosolized treatment fluid.

In certain embodiments, the handle of the rotary brush may be sealed outside of the enclosure device. In this example embodiment, the brush head may include a rotary shaft long enough to extend into the enclosure device, such that the brush head interface is located outside of the enclosure device, while the bristles are located inside the enclosure device. In this example embodiment, the enclosure device may seal around the rotary shaft, thereby containing the fluid and aerosolization created by the fluid delivery device, after the biofilm attached to the wound has been disrupted by the brush head.

In further embodiments, the handle of the rotary brush may be sealed outside of the enclosure device, while the brush head interface and the brush head are sealed inside the enclosure device. In this example embodiment, the enclosure device may seal around the rotary brush, such that the control mechanism and any brush controls that the rotary brush may have are sealed outside of the enclosure device. This example embodiment allows an operator to access the control mechanism and any brush controls outside of the enclosure device, while containing the fluid and aerosolization created by the fluid delivery device after the biofilm attached to the wound has been disrupted by the brush head.

At step 740, the rotary brush is controlled using a control unit. For example, a user may set a desired spin rate for a brush head using the control unit. The desired spin rate may depend on a variety of factors, such as the type of wound being clean, the material the bristles are made from, the diameter of each of the bristles, the bristle density of the brush head, the length of the bristles on the brush head, and the diameter of the brush head. It should be noted that, in certain embodiments, a separate control unit is not needed to control the spin rate of the brush head, as the rotary brush may include controls, such as the embodiment shown in FIG. 7.

At step 750 the wound is brushed using the rotary brush. In certain embodiments, the rotary brush can be used for the mechanical debridement of bacterial biofilm and wound slough that are present in chronically infected and inflamed wounds. In certain embodiments, the rotary brush has the ability to disrupt the biofilm attachment while preserving the integrity of the underlying wound tissue without a risk of injury to the wound.

In certain embodiments, at step 750 the rotary brush may be used to spin a brush head, having bristles with a specified stiffness and having a specified bristle density, at a specified rotary speed. For example, a specific brush head may be spun at a specific rotary speed, and may be applied to a wound at a specific pressure such that the brush head will disrupt the biofilm and debris without damaging the wound or the soft tissue surrounding the wound. In certain embodiments, spinning the brush head at a faster spin rate will result in a great force being applied to the biofilm than the same brush head would apply to biofilm at a lower spin rate. Further, using bristles with a higher stiffness will result in a greater force being applied to the biofilm. Generally speaking, bristles with a larger diameter will have a higher stiffness than bristles with a smaller diameter. Additionally, the stiffness of a bristle may depend on the material the bristle is made from. In certain embodiments, the stiffness of the bristles, the spin rate of the brush head, the bristle density, and the pressure to be applied to the wound may all be predetermined. In certain embodiments, biofilm may be removed from a wound, without damaging the wound, using a brush head having nylon bristles of twenty-five microns while spinning the brush head at a speed up to 800 RPM. An example of predetermining the above identified variables is discussed further herein.

At step 760, the wound is rinsed using the fluid delivery device. In certain embodiments, the fluid delivery system may be used as a mechanical debridement system that utilizes a jet lavage irrigation pump. In this example embodiment, the fluid delivery system cleans the wound with pressurized fluid, such as water or saline solution. In certain embodiments, the wound may be completely surrounded by an enclosure device secured to the skin surrounding the wound, such that the fluid irrigants used to debride the wound, and all of the other debris from the cleaning of the wound, will be collected and secured within the enclosure device. Further, step 760 may include a suction device used to suck out any fluid and/or debris that are collected within the enclosure device.

In addition to the above identified steps, the method of cleaning a wound 700 may also include delivery of other treatment modalities such as pressurized air flow $CO_2$ irrigant, antibiocidal solutions, and surfactant solutions. It should be appreciated that the method of cleaning a wound 700 may be accomplished using any of the above identified tools, and any combination thereof. Further, the method of cleaning a wound 700 may be accomplished using a tower based device that would have multiple facets, including a custom surgical tubing and hand piece set, digital electronic mechanisms, and foot pedal controls. This system may simplify and markedly reduce costs of delivery.

In certain embodiments, certain characteristics of the brush head, the desired spin rate of the brush head, and the optimal downward pressure to be applied to the wound may be predetermined based on the concept that an optimal shear force is needed to disrupt the biofilm attachment to the underlying surface without disrupting or damaging the underlying wound granulation tissue.

In certain embodiments, biofilm may be modeled as a non-deformable, rigid material. In this example embodiment, combining biofilm deformation with stresses for surface detachment assumes a deformable structure that remains quasi-static. Further, the elastic, viscoelastic, or plastic properties of biofilm may be described by realistic values. Generally, Young's elastic modulus for bacterial biofilms associated with the clinical model range from 0.03 to 0.35 MPa with an overall biofilm range of 0.03 to 0.7 MPa. In embodiments using nylon bristles with an elastic modulus ranging from 1-2 MPa, the brush head will have a general material stiffness that exceeds the biofilm.

In certain embodiments, the Young's modulus of the brush fibril of polypropylene or nylon at 1500-2000 MPa is marginally stiffer than that of biofilm at 0.07-0.7 MPa. The hardness of biofilm ranges from 0.79 to 14 kPa. In certain embodiments, the rotary brush bristles are made of polypropylene or nylon and measure 20 to 350 microns.

In the Semmes Weinstein (S-W) medical device for neurological sensation assessment, single brush bristles are used that are 110 microns (0.01 gram of direct force) to 350 microns (2 grams of direct force) applied to the human tissues. In certain embodiments, the amount of force needed for granulation tissue protection is the lowest level that adequately removes biofilm. Clinically, patients with mild neuropathy would not sense direct pressure of the S-W bristles at the 2 grams of force level.

In certain embodiments, the Archard abrasion equation may be used to assess the effects of a brush head on the granulation tissue surface, as shown below:

$$Q = \frac{KWL}{H}$$

And:

$$W = \frac{\pi^3 E r^4}{8L^2}$$

Where:

Q=total volume of wear debris produced

K=a dimensional constant

W=total normal load

L=sliding distance

H=hardness of the softest contacting surfaces; (biofilm=0.79 to 17 kPA)

Typically for mild wear, K=10-8; severe wear, K=10-2

This relationship is combined with the Force-Euler Buckling Equation to describe the effect of load to maximum buckling to the brush bristle. In this equation, $$F = \frac{\pi^2 EI}{(KL)^2}$$

and $$I = \pi/2r^4$$

and $$F = \frac{\pi^3 E r^4}{8L^2}$$

Where:

F=critical maximal force of load on a verticle column

E=modulus of elasticity

I=smallest area (second moment of inertia) of the cross section of the column; column center L=unsupported length of the column K=column effective length and depends on one end fixed and the other free to move; K=2.0

KL=effective length of the column

Combining the formulas will result in:

$$Q = \frac{\pi^3 E_{bristle} r^4_{bristle} K L_{sliding} N_{bristles}}{8L^2_{bristle} H_{biofilm}}$$

Where: (variables)

K=1E-08, wear amount $H_{biofilm}$=0.014 MPa $E_{bristle}$=2000 MPa, modulus of elasticity of nylon bristle $L_{sliding}$=distance traveled of a point at the periphery of the brush bristle circular mass with specified rotations of brush over time $D_{bristle}$=diameter of the brush bristle bundle $L_{bristle}$=length of bristle from proximal fixed brush attachment to free tip of bristle $N_{bristles}$=number of bristles Q=total volume of material removed in $mm^3$ Example 1: (Small Brush)

Where:

$$K = 1E\text{-}08$$

$$H_{biofilm} = 0.014\ MPa$$

$$E_{bristle} = 2000\ MPa$$

$$L_{sliding} = 114906\ \text{mm.}(78.8\ \text{mm circumference} * 800\ \text{RPMs} * 2\ \text{minutes})$$

$$r^4 = 2.08E-08$$

$$\pi^3 = 31$$

$$L_{bristle} = 23\text{-}29\ \text{mm}$$

$$Q = 0.4\ \text{mm}^3$$

Example 2: (Large Brush)

Where:

$$K = 1E - 08$$

$$H_{biofilm} = 0.014\ MPa$$

$$E_{bristle} = 2000\ MPa$$

$$L_{sliding} = 242581\ \text{mm.}(151.6\ \text{mm circumference} * 800\ \text{RPMs} * 2\ \text{minutes})$$

$$r^4 = 2.08E - 08$$

$$\pi^3 = 31$$

$$L_{bristle} = 23\text{-}29\ \text{mm}$$

$$Q = 3.87\ \text{mm}^3$$

In certain embodiments, the force exerted by each bristle is the same on the surface of the granulation tissue. However, the amount of total overall force onto the surface increases with increased brush head diameter. This is, in part, due to the amount of area increasing, the number of bristles increasing, and the amount of sliding for bristles on the periphery of the brush head versus that in the center of the brush head. In certain embodiments, the total amount of force could be reduced by spinning the brush at a lower rotational speed, or by lowering the bristle density (i.e. more sparsely arranged bristles).

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using one or more separate intervening members, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It is important to note that the construction and arrangement of the system as shown in the various exemplary embodiments is illustrative only. Additionally, any element disclosed in one embodiment may be incorporated or utilized with any other embodiment disclosed herein. Although only one example of an element from one embodiment that can be incorporated or utilized in another embodiment has been described above, it should be appreciated that other elements of the various embodiments may be incorporated or utilized with any of the other embodiments disclosed herein.

What is claimed is:

1. A wound care system, comprising:

a rotary brush configured to brush a soft-tissue wound to detach a biofilm from a surface of the soft-tissue wound, the rotary brush including:

a body including a handle and a brush head interface; and a plurality of interchangeable brush heads selectable based on features of the soft-tissue wound, each brush head including:

a plurality of bristles each having an elastic modulus ranging from 1-2 MPa, a diameter ranging from 22-26 microns, and a length ranging from 23 to 29 mm, wherein the plurality of bristles cover a brush area of the brush head in the range of 1500 $\text{mm}^2$ to 7500 $\text{mm}^2$, and wherein the diameter remains substantially uniform along the entire length of each bristle;

a rotary shaft having a length ranging from 1 inch to 8 inches, the rotary shaft configured to engage with the brush head interface to couple the brush head with the body, wherein the plurality of interchangeable brush heads differ from one another in at least one of bristle diameter, bristle length, brush area, or rotary shaft length;

a fluid delivery device separate from and external to the body of the rotary brush, the fluid delivery device configured to rinse the soft-tissue wound; and a control unit coupled to the rotary brush via a first conduit and to the fluid delivery device via a second conduit, the control unit separate from and external to the body of the rotary brush and the fluid delivery device and configured to:

operate the rotary brush at a first spin rate from a plurality of available spin rates; and operate the fluid delivery device at a first fluid flow rate from a plurality of available flow rates, wherein the rotary brush, the fluid delivery device, and the control unit are each discrete devices that do not share a common housing.

2. The wound care system of claim 1, further comprising:

an adhesive configured to secure an enclosure device to a portion of skin such that the enclosure device surrounds the soft-tissue wound; and wherein the enclosure device is configured to receive at least a portion of at least one of the rotary brush or the fluid delivery device.

3. The wound care system of claim 1, wherein the control unit is configured to cause the rotary brush to spin at a rate of 750-850 rotations per minute.

4. The wound care system of claim 1, wherein the rotary brush is an electric powered rotary brush.

5. The wound care system of claim 2, wherein the rotary brush comprises a brush head received by the body.

6. The wound care system of claim 5, wherein inserting at least a portion of the rotary brush into the enclosure device comprises inserting only the brush head into the enclosure device.

7. The wound care system of claim 6, wherein inserting at least the portion of the rotary brush into the enclosure device comprises inserting the brush head and a portion of the body into the enclosure device such that a remaining portion of the body and the handle remain outside of the enclosure device and may be grasped by a user.

8. The wound care system of claim 1, wherein the plurality of bristles are made from nylon.

9. The wound care system of claim 1, further comprising:

a force sensor configured to measure a force on a brush head of the plurality of interchangeable brush heads, wherein the control unit is configured to receive data indicative of the force from the force sensor and cease rotation of the brush head based on the force being greater than a predefined threshold.

10. The wound care system of claim 1, wherein a brush head of the plurality of interchangeable brush heads further comprises a first bristle and a second bristle of the plurality of bristles, the first bristle positioned at a first end of the brush head and having a first length, the second bristle positioned at a second end of the brush head and having a second length, wherein the first length is greater than the second length.

11. The wound care system of claim 1, wherein the plurality of interchangeable brush heads further comprises a first brush head with a first bristle density and a second brush head with a second bristle density, wherein the first bristle density is less than the second bristle density.

12. A wound care system, comprising:

a rotary brush configured to brush a soft-tissue wound to detach a biofilm from a surface of the soft-tissue wound, wherein the rotary brush has a body including a handle, a brush head interface, and a plurality of interchangeable brush heads selectable based on features of the soft-tissue wound, each brush head including:

a plurality of bristles each having a diameter between 22-26 microns and a length ranging from 23 to 29 mm, and having an elastic modulus ranging from 1-2 MPa, wherein the plurality of bristles cover a brush area of the brush head in the range of 1500 $mm^2$ to 7500 $mm^2$, and wherein the diameter remains substantially uniform along the entire length of each bristle;

a rotary shaft having a length ranging from 1 inch to 8 inches, the rotary shaft configured to engage with the brush head interface to couple the brush head with the body, wherein the plurality of interchangeable brush heads differ from one another in at least one of bristle diameter, bristle length, brush area, or rotary shaft length;

a fluid delivery device, separate from and external to the body of the rotary brush, configured to rinse the soft-tissue wound; and a control unit coupled to the rotary brush via a first conduit and to the fluid delivery device via a second conduit, the control unit separate from and external to the body of the rotary brush and the fluid delivery device and configured to:

operate the rotary brush at a first spin rate from a plurality of available spin rates; and operate the fluid delivery device at a first fluid flow rate from a plurality of available flow rates, wherein the rotary brush, the fluid delivery device, and the control unit are each discrete devices that do not share a common housing.

13. The wound care system of claim 12, wherein the plurality of bristles are made of nylon.

14. The wound care system of claim 12, wherein the elastic modulus of the plurality of bristles exceeds a material stiffness of a biofilm.

15. The wound care system of claim 12, further comprising:

a force sensor configured to measure a force on a brush head of the plurality of interchangeable brush heads, wherein the control unit is configured to receive data indicative of the force from the force sensor and cease rotation of the brush head based on the force being greater than a predefined threshold.

16. The wound care system of claim 12, wherein a brush head of the plurality of interchangeable brush heads further comprises a first bristle and a second bristle of the plurality of bristles, the first bristle positioned at a first end of the brush head and having a first length, the second bristle positioned at a second end of the brush head and having a second length, wherein the first length is greater than the second length.

17. The wound care system of claim 12, wherein the plurality of interchangeable brush heads further comprises a first brush head with a first bristle density and a second brush head with a second bristle density, wherein the first bristle density is less than the second bristle density.

* * * * *